United States Patent
Yost et al.

(10) Patent No.: US 6,343,513 B1
(45) Date of Patent: Feb. 5, 2002

(54) NON-DESTRUCTIVE EVALUATION METHOD AND APPARATUS FOR MEASURING ACOUSTIC MATERIAL NONLINEARITY

(75) Inventors: William T. Yost, Newport News; John H. Cantrell, Williamsburg, both of VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 09/616,346

(22) Filed: Jul. 14, 2000

Related U.S. Application Data

(60) Provisional application No. 60/143,841, filed on Jul. 15, 1999.

(51) Int. Cl.[7] .............................. G01H 1/00; G01M 7/00
(52) U.S. Cl. .............................. 73/645; 73/577; 73/1.82
(58) Field of Search ........................ 73/1.82, 645, 579, 73/577

(56) References Cited

U.S. PATENT DOCUMENTS

| | | | |
|---|---|---|---|
| 4,649,750 A | * 3/1987 | Cantrell, Jr. et al. | .......... 73/599 |
| 5,325,339 A | * 6/1994 | Yost et al. | ................ 367/13 |
| 5,566,573 A | * 10/1996 | Yost | ................ 73/646 |
| 6,197,130 B1 | * 3/2001 | Cantrell et al. | ............ 148/508 |

* cited by examiner

Primary Examiner—Richard A. Moller
(74) Attorney, Agent, or Firm—Helen M. Galus

(57) ABSTRACT

An acoustic non-linearity parameter ($\beta$) measurement method and system for Non-Destructive Evaluation (NDE) of materials and structural members obviates the need for electronic calibration of the measuring equipment. Unlike known substitutional measuring techniques requiring elaborate calibration procedures, the electrical outputs of the capacitive detector of a sample with known $\beta$ and the test sample of unknown $\beta$ are compared to determine the unknown $\beta$. In order to provide the necessary stability of the present-inventive reference-based approach, the bandpass filters of the measurement system are maintained in a temperature-controlled environment, and the line voltage supplied to said amplifiers is well-regulated.

20 Claims, 4 Drawing Sheets

NON-DESTRUCTIVE EVALUATION METHOD AND APPARATUS FOR MEASURING ACOUSTIC MATERIAL NONLINEARITY

CLAIM OF BENEFIT OF PROVISIONAL APPLICATION

Pursuant to 35 U.S.C. §119, the benefit of priority from provisional application 60/143,841, with a filing date of Jul. 15, 1999, is claimed for this non-provisional application.

ORIGIN OF THE INVENTION

The invention described herein was made by employees of the U.S. Government and may be manufactured and used by or for the Government for governmental purposes without the payment of any royalties thereon or therefore.

BACKGROUND OF THE INVENTION

1. Field of the Invention

The present invention generally relates to ultrasonic measurement techniques for non-destructive evaluation of materials and structural members, including the determination of fatigue damage.

2. Background

Non-Destructive Evaluation (NDE) of materials involves the inspection of materials without having to damage the materials or dismantle structures to which the materials are incorporated. Among the many important NDE operations are the inspection of aircraft, bridge and building structural members to detect fatigue damage that could possibly lead to catastrophic failure.

Known methods of fatigue damage detection include bombarding material under test with acoustic finite amplitude waves and examining the response waves (including the fundamental and harmonics) produced by the material to determine a nonlinearity parameter ($\beta$) which may be correlated to material fatigue. See, pending U.S. patent application Ser. No. 09/065,986, filed Apr. 24, 1998, entitled "Method and Apparatus to Assess Optimum Strength During Processing of Precipitation Strengthened Alloys", which is hereby incorporated herein by reference as if set forth in its entirety. Among the critical shortcomings of known ultrasonic fatigue damage test methods (such as dye penetrant techniques) and systems is the inability of those approaches to detect material damage such as internal cracks and other important internal eccentricities.

Other restrictions of known acoustic nonlinearity parameter measurement techniques make such techniques less than ideal for field testing. For example, "direct substitutional" techniques require extensive electronic calibration of the measuring equipment prior to use in order to accurately measure response wave amplitudes necessary for calculating the $\beta$.

SUMMARY OF THE INVENTION

In view of the aforementioned problems and deficiencies of the known art, the present invention provides a method of measuring acoustic nonlinearity in materials. The method at least includes the steps of a) generating and applying an acoustic signal to a reference material having a known acoustic non-linearity parameter ($\beta$), and b) applying an output signal from the reference material and derived from the acoustic signal generated in step a) to at least one environmentally controlled bandpass amplifier. The method also at least includes the steps of c) generating and applying an acoustic signal to a sample material, d) applying an output signal from the sample material and derived from the acoustic signal generated in step c) to at least one environmentally controlled bandpass amplifier, e) comparing the outputs of the bandpass amplifiers in steps b) and d), and f) based upon the comparison in step e), determining the $\beta$ of the sample material.

The present invention also provides a system adapted to measure nonlinearity in materials, at least including an acoustic signal generator adapted to generate and apply acoustic signals to a reference material having a known acoustic non-linearity parameter ($\beta$) and a sample material with an unknown $\beta$, and an acoustic signal detector adapted to be coupled to the reference material and to the sample material, and adapted to apply an output signal from the reference and sample materials derived from the acoustic signals generated by the acoustic signal generator to at least one environmentally controlled bandpass amplifier. The system also at least includes a comparator adapted to compare the outputs of the bandpass amplifier derived from the reference material and the sample material, and an acoustic non-linear parameter calculator coupled to the output of the comparator adapted to determine the $\beta$ of the sample material.

BRIEF DESCRIPTION OF THE DRAWING FIGURES

Features and advantages of the present invention will become apparent to those skilled in the art from the description below, with reference to the following drawing figures, in which.

DESCRIPTION OF THE PREFERRED EMBODIMENTS

The description below details the present-inventive reference-based acoustic measuring system and technique. General discussions of acoustic wave testing for fatigue determination can be found in the following U.S. Patents, all of which name one or both of the inventors for the present letters patent, and the reader is therefore so referred for background material as well as methods and apparatus which may be utilized with the present invention: U.S. Pat. No. 4,649,750; 5,566,573; and 5,325,339, and these patents are hereby incorporated by reference as set forth in their entirety herein.

Figure 1:
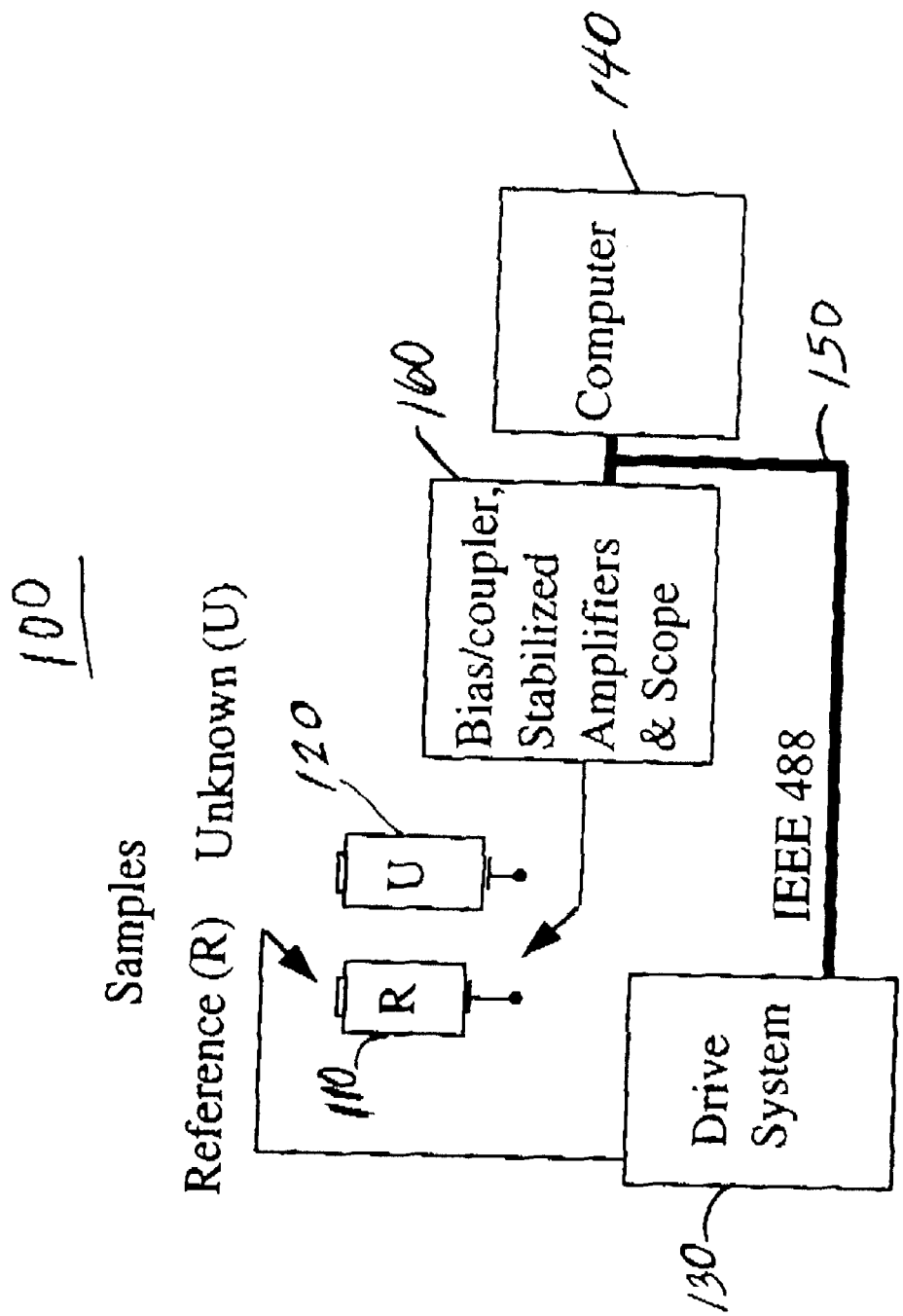
FIG. 1 is a schematic block diagram of the present-inventive reference-based measurement system 100.

FIG. 1 illustrates a basic schematic diagram of the present-inventive reference-based acoustic measuring system 100. In the system using the present-inventive method associated therewith, a drive system 130 subjects the test material (reference or sample) to acoustic compressional waves of finite amplitude. The drive system 130 contains a tone burst generator (not shown in FIG. 1, but analogous to the one 234 in FIG. 2) such as the Hewlett-Packard Model 3314A used in the preferred embodiment to produce a series of sequential amplitude tone bursts, for example, increasing amplitude tone bursts. A capacitive detector (not shown in FIG. 1, but analogous to the one 210 in FIG. 2) convert the response acoustic waves of a reference material 110 of known nonlinearity parameter β and the response acoustic waves of a sample material for which the β is unknown, into an alternating current (AC) electrical signal. In an alternate embodiment, the capacitive detector can be replaced by a prior art contact transducer.

A unit 160 receives the output of the capacitive detector. A bias/coupler (not shown in FIG. 1, but analogous to the one 262 in FIG. 2) separates the AC signal of the capacitive detector from the capacitive detector's direct current (DC) bias voltage. The resulting AC signal is amplified by one or more bandpass amplifiers (not shown in FIG. 1, but analogous to the ones 266 in FIG. 2) digitized, and passed to a digital oscilloscope (not shown in FIG. 1, but analogous to the one 268 in FIG. 2) such as the LeCroy Model 9430 used in the preferred embodiment. A computer 140 receives the output of the oscilloscope and compares the response signals for the reference and sample materials to calculate the nonlinearity parameter β of the sample material according to the following equation:

$$\beta_U = \beta_R * (\Gamma_{vU} M_{LU})/(\Gamma_{vR} M_{LR})$$

where $\beta_U$, is the unknown nonlinearity parameter, $\beta_R$ is the nonlinearity parameter of the reference material, $\Gamma_{vU}$ is the ratio of the second harmonic and fundamental voltage amplitude of the output of the bandpass amplifiers with respect to the sample material, $\Gamma_{vR}$ is the ratio of the second harmonic and fundamental voltage amplitude of the output of the bandpass amplifiers with respect to the reference material, and $M_{LU}$ and $M_{LR}$ are coefficients determined by a quadratic fit given by $8c^2/(\omega^2 a)$, where c is the infinitesimal wave speed, a is the Lagrangian material coordinate, and ω is the angular frequency.

Of great importance to the operation of the system 100 is the fact that the bandpass amplifiers are environmentally controlled, eliminating the need for pre-test calibrations of the measuring equipment. In the preferred embodiment, the environmental controls include constant temperature maintenance and amplifier line voltage stabilization.

Figure 2:
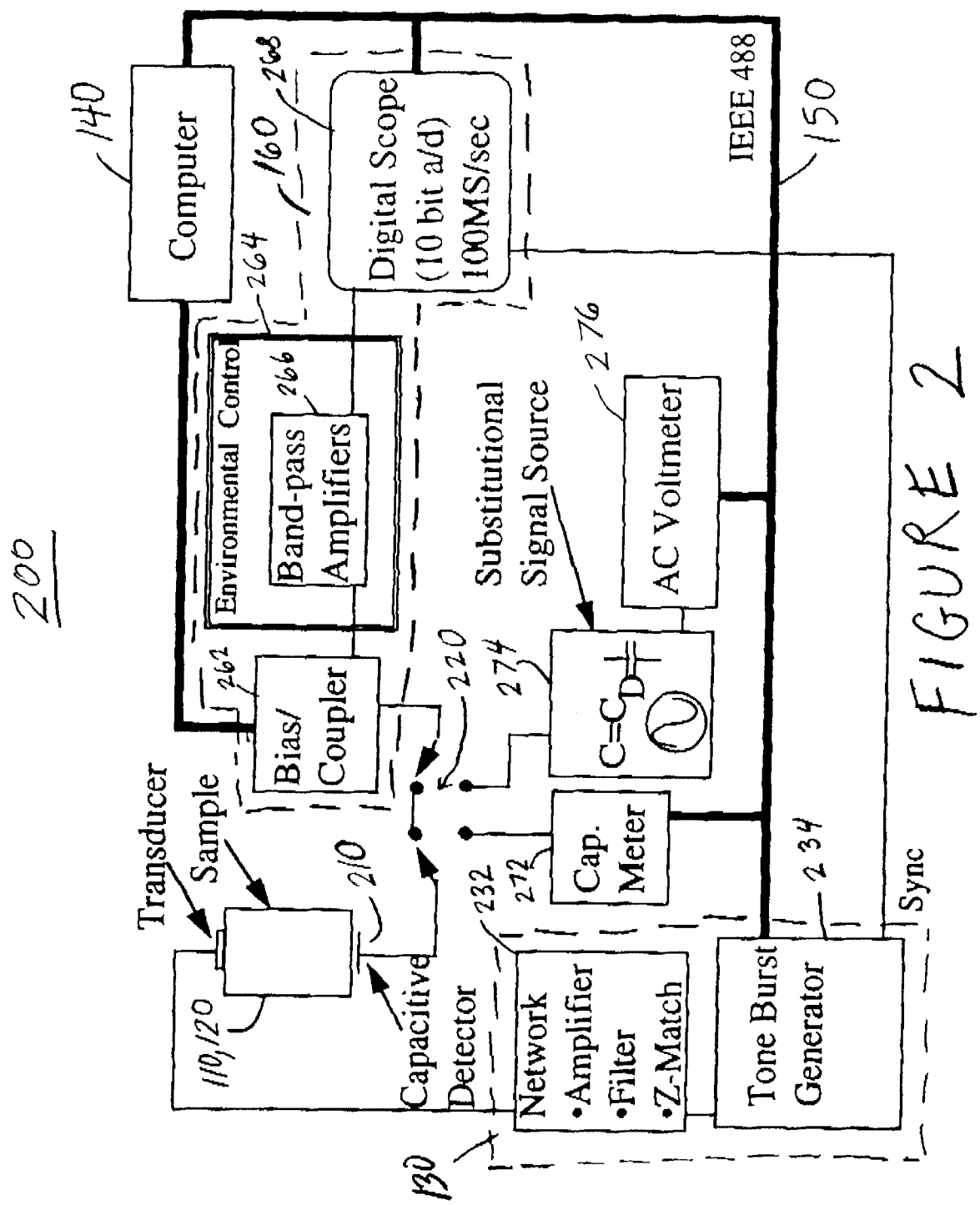
FIG. 2 is a schematic block diagram of a more detailed version 200 of the present-inventive reference-based measurement system 100.

FIG. 2 shows a more detailed version 200 of the system 100 in FIG. 1. The system 200 has already been substantially described with respect to FIG. 1. However, the preferred embodiment contains a few additional elements. The drive system 130 includes not only a tone burst generator 234, but also a network 232 for amplifying, filtering and impedance-matching of the tone burst signals. For purposes of comparisons, the system 200 also has a substitutional signal source 274. The system 200 also contains a capacitive meter 272 and an AC voltmeter 276.

Figure 3:
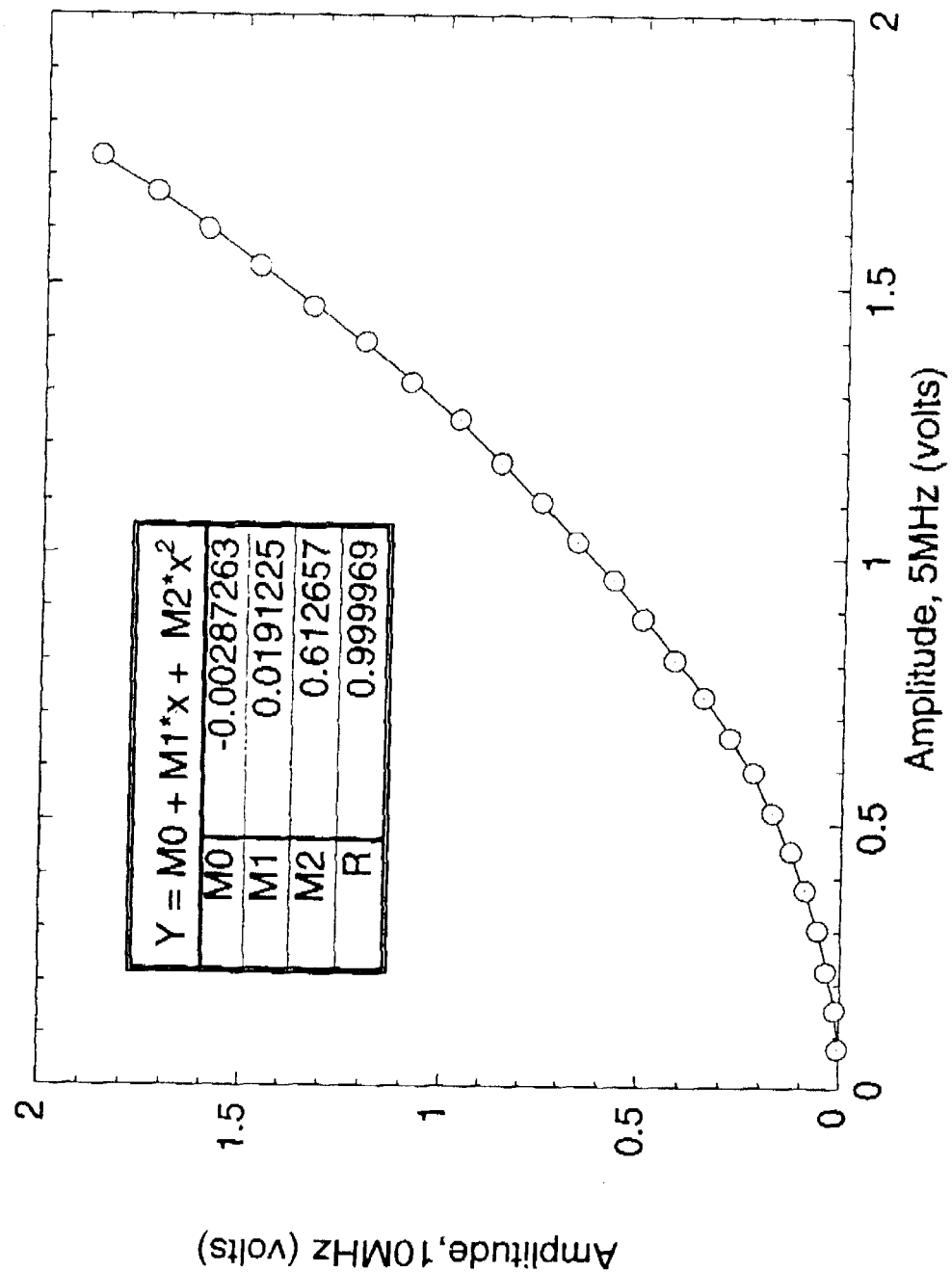
FIG. 3 is a plot of reference material harmonic amplitudes versus fundamental amplitudes.
Figure 4:
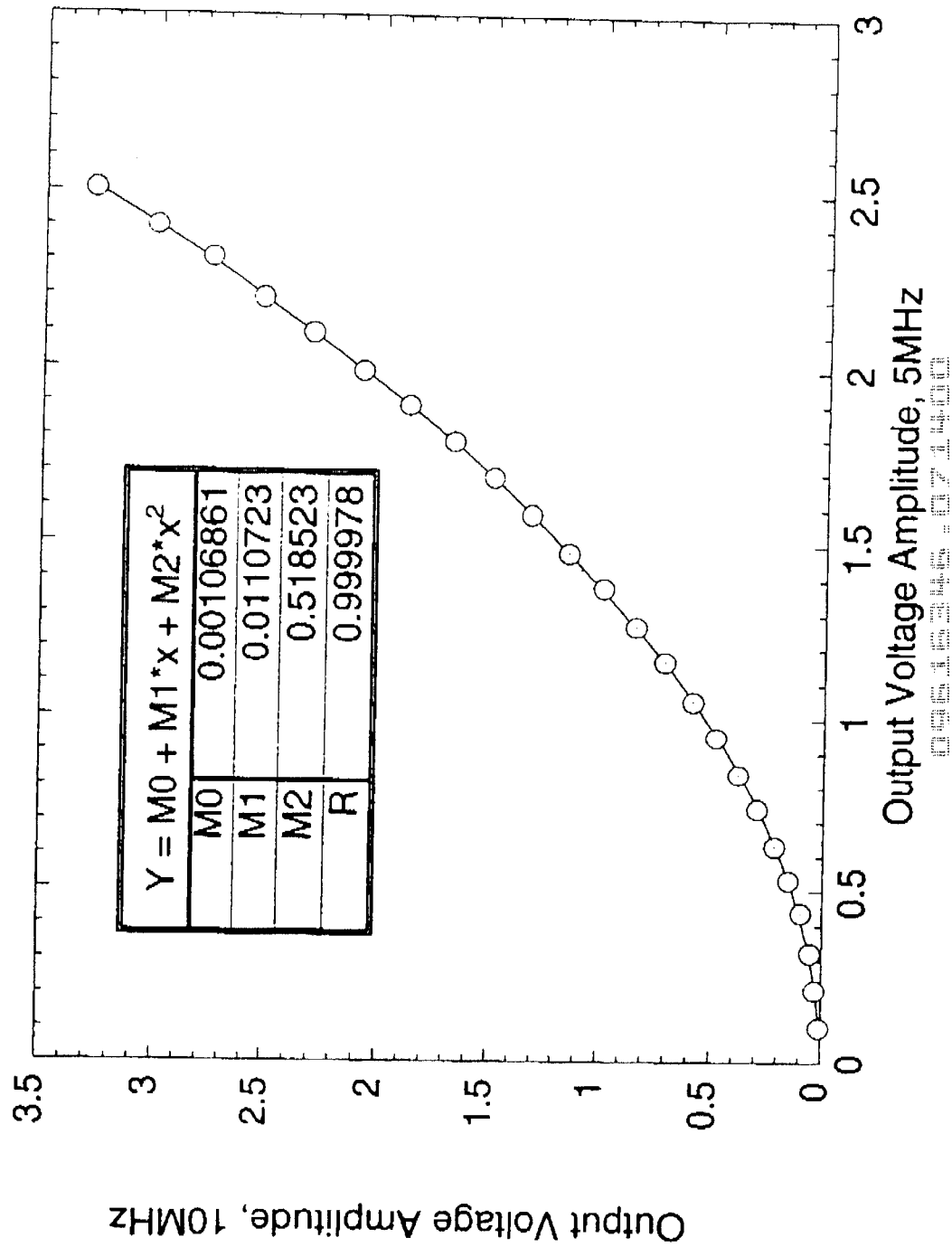
FIG. 4 is a plot of sample material harmonic amplitudes versus fundamental amplitudes.

FIGS. 3 and 4 show experimental data from a test using the present-inventive reference-based measuring technique. More particularly, FIG. 3 shows a plot of the amplitude of the responsive harmonic wave of the reference material versus its fundamental amplitude. FIG. 4 shows a plot of the amplitude of the responsive harmonic wave of the sample material versus its fundamental amplitude. It will be appreciated by those skilled in the art that the frequency of the harmonic waves is twice that of their fundamentals.

Table 1 shows that the experimental results of a test conducted by the inventors of the invention covered by this letters patent produce a high degree of correlation between the reference-based method of the present invention and known substitutional-based methods.

TABLE 1

| β measured by Substitutional Tech. | β measured by Ref. Meas. Tech. | Percent Difference |
|---|---|---|
| 8.077 | 8.188 | 1.4 |

Variations and modifications of the present invention are possible, given the above description. However, all variations and modifications which are obvious to those skilled in the art to which the present invention pertains are considered to be within the scope of the protection granted by this Letters Patent. Further, U.S. patent application Ser. No. 09/065,986 filed on Apr. 24, 1998, which has been incorporated in its entirety herein by reference, may contain methods and/or apparatus which might be used with the present invention.

What is claimed is:

1. A method of measuring acoustic nonlinearity in materials, said method comprising the steps of:
   a) generating and applying an acoustic signal to a reference material having a known acoustic non-linearity parameter (β);
   b) applying an output signal from said reference material and derived from said acoustic signal generated in step a) to at least one environmentally controlled bandpass amplifier;
   c) generating and applying an acoustic signal to a sample material;
   d) applying an output signal from said sample material and derived from said acoustic signal generated in step c) to at least one environmentally controlled bandpass amplifier;
   e) comparing the outputs of said bandpass amplifiers in steps b) and d); and
   f) based upon the comparison in step e), determining the β of said sample material.

2. The method in claim 1 wherein the environment controlled for said bandpass amplifiers comprises temperature.

3. The method in claim 1 wherein the environment controlled for said bandpass amplifiers comprises line voltage.

4. The method in claim 1 wherein the environment controlled for said bandpass amplifiers comprises temperature and line voltage.

5. The method in claim 1 further comprising the steps of detecting the acoustic outputs of said reference and sample materials via at least one capacitive detector.

6. The method in claim 1 further comprising the steps of detecting the acoustic outputs of said reference and sample materials via at least one contact transducer.

7. The method in claim 1 wherein said acoustic signals generated in steps a) and c) are tone bursts.

8. The method in claim 2 wherein said acoustic signals generated in steps a) and c) are tone bursts.

9. The method in claim 3 wherein said acoustic signals generated in steps a) and c) are tone bursts.

10. The method in claim 4 wherein said acoustic signals generated in steps a) and c) are tone bursts.

11. A system adapted to measure nonlinearity in materials, said system comprising:
    an acoustic signal generator adapted to generate and apply acoustic signals to a reference material having a known acoustic non-linearity parameter (β) and a sample material with an unknown β;

an acoustic signal detector adapted to be coupled to said reference material and to said sample material, and adapted to apply an output signal from said reference and sample materials derived from said acoustic signals generated by said acoustic signal generator to at least one environmentally controlled bandpass amplifier;

a comparator adapted to compare the outputs of said bandpass amplifier derived from said reference material and said sample material; and an acoustic non-linear parameter calculator coupled to the output of said comparator adapted to determine the $\beta$ of said sample material.

12. The system in claim 11 wherein the environment controlled for said bandpass amplifiers comprises temperature.

13. The system in claim 11 wherein the environment controlled for said bandpass amplifiers comprises line voltage.

14. The system in claim 11 wherein the environment controlled for said bandpass amplifiers comprises temperature and line voltage.

15. The system in claim 11 wherein said acoustic signal detector is a capacitive detector.

16. The system in claim 11 wherein said acoustic signal detector is a contact transducer.

17. The system in claim 11 wherein said acoustic signals generated by said acoustic signal generator are tone bursts.

18. The system in claim 12 wherein said acoustic signals generated by said acoustic signal generator are tone bursts.

19. The system in claim 13 wherein said acoustic signals generated by said acoustic signal generator are tone bursts.

20. The system in claim 14 wherein said acoustic signals generated by said acoustic signal generator are tone bursts.

* * * * *